(12) United States Patent
Ninomiya et al.

(10) Patent No.: US 8,095,194 B2
(45) Date of Patent: Jan. 10, 2012

(54) PROBE DEVICE

(75) Inventors: Atsushi Ninomiya, Ome (JP); Yoshimi Kasai, Nagareyama (JP)

(73) Assignee: Hitachi, Ltd., Tokyo (JP)

( * ) Notice: Subject to any disclaimer, the term of this patent is extended or adjusted under 35 U.S.C. 154(b) by 623 days.

(21) Appl. No.: 12/193,131

(22) Filed: Aug. 18, 2008

(65) Prior Publication Data
US 2009/0088649 A1 Apr. 2, 2009

(30) Foreign Application Priority Data
Sep. 28, 2007 (JP) ................... 2007-253025

(51) Int. Cl.
*A61B 5/00* (2006.01)
*A61B 6/00* (2006.01)

(52) U.S. Cl. .............. 600/310; 600/473; 600/476

(58) Field of Classification Search ............ 600/310, 600/344, 473, 476
See application file for complete search history.

(56) References Cited

U.S. PATENT DOCUMENTS

| | | | | |
|---|---|---|---|---|
| 6,332,092 | B1 * | 12/2001 | Deckert et al. | 600/476 |
| 7,139,600 | B2 * | 11/2006 | Maki et al. | 600/344 |
| 2008/0183055 | A1 * | 7/2008 | Ninomiya et al. | 600/310 |
| 2009/0247839 | A1 * | 10/2009 | Ninomiya et al. | 600/310 |

FOREIGN PATENT DOCUMENTS

| | | |
|---|---|---|
| EP | 1 374 778 | 1/2004 |
| EP | 1 938 746 | 7/2008 |
| JP | 2001-286449 | 10/2001 |
| WO | WO 00/45701 | 8/2000 |

* cited by examiner

*Primary Examiner* — Michael Rozanski
(74) *Attorney, Agent, or Firm* — Antonelli, Terry, Stout & Kraus, LLP.

(57) ABSTRACT

A probe device includes a sheet-like probe holder, a plurality of light-emitting probes and a plurality of detection probes mounted on the probe holder at a predetermined interval, a sheet holding unit holding the probe holder at a predetermined position on the biological surface, and a fixing band mounting the sheet holding unit on the living body. Each of the plurality of light-emitting probes and the detection probes includes a probe body including a light emitting unit or a detection unit, and a probe mounting part detachably mounting the probe body to the probe holder at a predetermined position.

3 Claims, 12 Drawing Sheets

PROBE DEVICE

CLAIM OF PRIORITY

The present application claims priority from Japanese patent application JP2007-253025 filed on Sep. 28, 2007, the content of which is hereby incorporated by reference into this application.

FIELD OF THE INVENTION

The present invention relates to a probe device for a biological light measuring apparatus, and more particularly, to a probe device for a biological light measuring apparatus that is suitable for measuring the change of a dynamic state of blood in a local living body.

DESCRIPTION OF RELATED ART

A measurement apparatus, which is called an optical topography apparatus, has been known as a biological light measuring apparatus. In this measurement apparatus, a probe device, which includes a plurality of probe bodies each including radiation/detection parts, is mounted so that each of the probe bodies comes in close contact with a measured portion, for example, a head, and near infrared light is radiated from each of the probe bodies, so as to perform measurement.

In a probe device in the related art, a plurality of probe bodies are disposed in a lattice on a shell, which is formed of a sheet in a bowl shape so as to correspond to the shape of the head of the subject. Each of the probe bodies is detachable from the shell. When it is confirmed on a screen of a monitor that the probe bodies imperfectly come in contact with a scalp due to hair, it is possible to remount only the probes that imperfectly come in contact with the scalp. When being mounted on the head of the subject, the probe device having the above-mentioned structure is not necessarily fitted to the head due to the individual difference in the shape of the head of the subject or the difference in the portion to be mounted. For this reason, the probe device is used while a fixing belt is fastened to the jaw so that the shell is satisfactorily pressed against the head. During the measurement, near infrared light transmitted through each optical fiber is radiated under the skin of the head by the radiation probe bodies, and the reflected light is received by the receiving probe bodies and then transmitted to a measurement apparatus body through the optical fibers. This is disclosed, for example, in JP-A-2001-286449.

In the probe device in the related art, light emitting parts for radiating light onto the shell and detection parts are alternately arranged in a lattice, and the light emitting parts and the detection parts have a structure supplying light through the optical fibers or collecting detected light through the optical fibers, respectively. Accordingly, a plurality of fibers are mounted around the head of the subject, who puts on the probe device on one's head. For this reason, there is a problem in that the subject's degree of freedom in action is restricted or the subject has a feeling of insecurity.

BRIEF SUMMARY OF THE INVENTION

An object of the invention is to provide a probe device that improves inspection accuracy and is easily mounted on a subject.

In order to achieve the above-mentioned object, according to the invention, there is provided a probe device that includes a sheet-like probe holder, a plurality of light-emitting probes and a plurality of detection probes which are mounted on the probe holder at a predetermined interval, a sheet holding unit holding the probe holder at a predetermined position on a biological surface, and a fixing band that mounts the sheet holding unit on a living body. Each of the plurality of the light-emitting probes and the detection probes includes a probe body that includes a light emitting unit or a detection unit, and a probe mounting part that detachably mounts the probe body to the probe holder at a predetermined position. The sheet holding unit surrounds the periphery of the probe holder, and has a predetermined gap between the probe holder and the biological surface so as to form a light-shielded space where light is shielded. The probe body includes a main protrusion provided with a light transmission unit and a plurality of sub-protrusions disposed around the main protrusion, at one end thereof. The probe mounting part holds the probe body rotatabley around the main protrusion so that one end of the probe body including the main protrusion and the sub-protrusions is exposed in the light-shielded space and the other end of the probe body is exposed to the outside of the probe holder, and a protruding portion of the probe holder protruding toward the light-shielded space is larger than a protruding portion of the probe holder protruding toward the outside.

According to the invention, a probe device can improve inspection accuracy by changing the posture of the probe body through a light-shielded space where light is shielded that has a predetermined gap, and be easily mounted on a subject.

Other objects, features and advantages of the invention will become apparent from the following description of the embodiments of the invention taken in conjunction with the accompanying drawings.

BRIEF DESCRIPTION OF THE SEVERAL VIEW OF THE DRAWING

DETAILED DESCRIPTION OF THE INVENTION

A biological light measuring apparatus according to an embodiment of the invention will be described in detail below with reference to FIGS. 1A to 12B. In the biological light measuring apparatus according to the embodiment, the local change of a dynamic state of blood in a living body is measured by using a fact that, when a portion in a brain acts, the amount of blood is increased for supplying oxygen to the portion in the brain. Specifically, the change in the amount of blood near the surface of the cerebrum is measured by radiating near infrared light on a scalp and measuring the diffusion of the near infrared light that is caused by hemoglobin of blood, and is displayed on a two-dimensional map or the like. Accordingly, it is possible to easily observe the action of the brain. In this case, the near infrared light is an electromagnetic wave that has a wavelength longer than that of visible light.

Figure 1A:
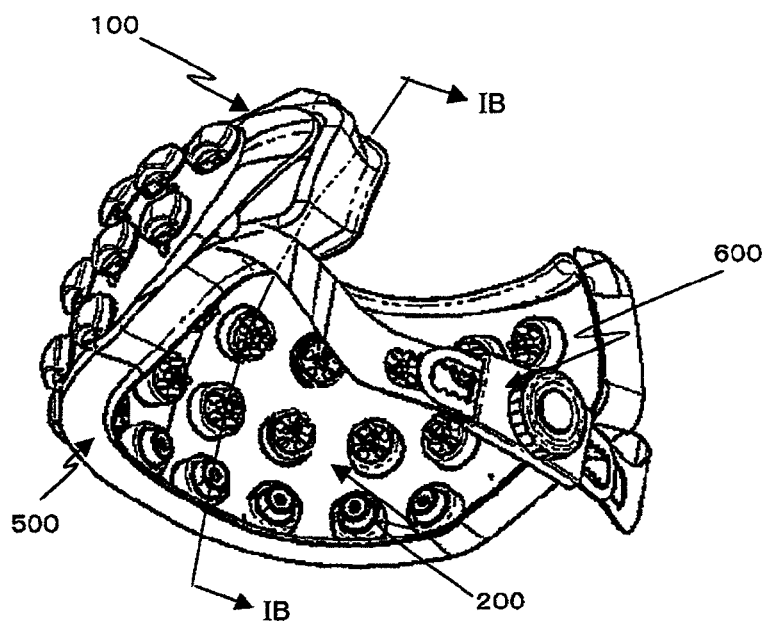
FIGS. 1A to 1C are view showing a schematic structure of a probe device according to an embodiment of the invention.
Figure 1B:
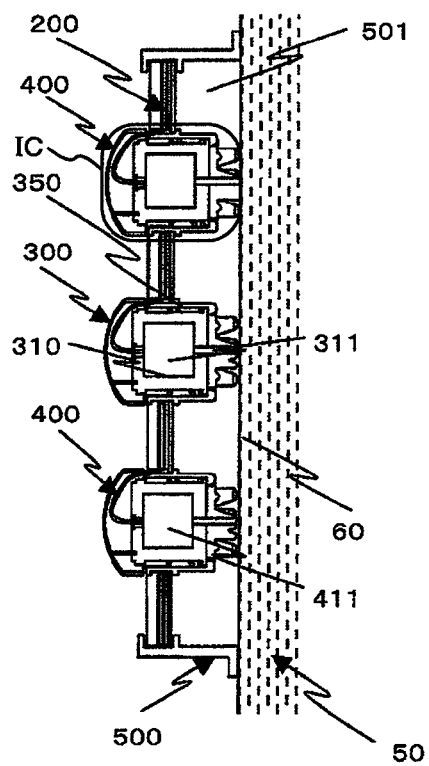
Figure 1C:
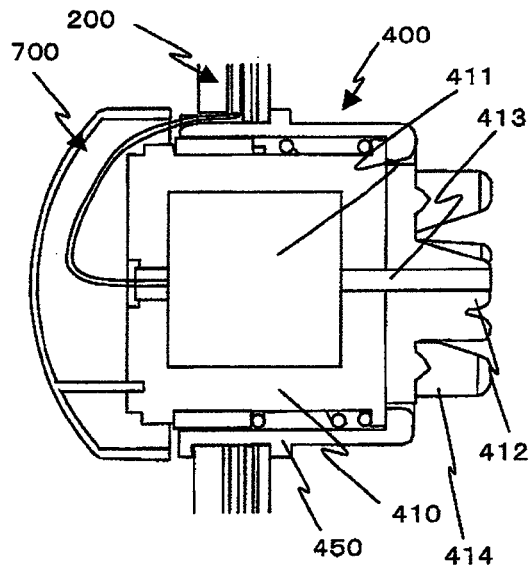

First, a schematic structure of a probe device of the biological light measuring apparatus according to this embodiment will be described with reference to FIGS. 1A to 1C. In this case, FIGS. 1A to 1C are view showing the schematic structure of the probe device according to this embodiment: FIG. 1A is an external perspective view of the probe device, FIG. 1B is a cross-sectional view taken along a line IB-IB of FIG. 1A, and FIG. 1C is an enlarged cross-sectional view of a probe that is a portion IC of FIG. 1A.

In FIGS. 1A to 1C, a probe device 100 of this embodiment includes a sheet-like probe holder 200, a plurality of light-emitting probes 300 and a plurality of detection probe 400 that are mounted on the probe holder 200 at predetermined intervals, a sheet holding unit 500 that holds the probe holder 200 at a predetermined position of a head of the subject (a portion to be inspected), and a fixing band 600 that fixes the sheet holding unit 500 to the subject.

The probe holder 200 is a laminated member formed by laminating a plurality of sheets including wiring sheets on which signal lines and power source lines are wired. The probe holder has a holding function that has flexibility for maintaining postures of the light-emitting probes 300 and the detection probes 400, a light shielding function that prevents external light from entering the head, and a wiring function that includes the wiring of the signal lines and the power source lines. That is, the probe holder 200 supports the plurality of light-emitting probes 300 and the plurality of detection probes 400 so that the detection probes 400 are positioned near both sides of the light-emitting probes 300 on the plane of the probe holder and the light-emitting probes and the detection probes are alternately arranged in a matrix. Further, the probe holder 200 has appropriate flexibility and strength that are required for maintaining the postures of two kinds of the probes, prevents the external light from entering the portion to be inspected, and ensures breathability for sweating.

The light-emitting probes 300 and the plurality of detection probes 400 have the same structure as shown in FIG. 1C. The structure of the detection probe 400 will be mainly described herein, and the difference between the detection probe 400 and the light-emitting probe 300 will be mainly described for the light-emitting probe 300.

As shown in FIG. 1C, the detection probe 400 includes a detection probe body 410 that is provided with a detection unit 411, and a detection probe mounting part 450 that mounts the detection probe body 410 at a predetermined position on the probe holder 200. Meanwhile, the light-emitting probe 300 includes a light-emitting probe body 310 that includes a light emitting unit 311 having the same structure as the detection unit 411, and a light-emitting probe mounting part 350 that mounts the light-emitting probe body 310 at a predetermined position on the probe holder 200. In addition, the detection and light-emitting probe bodies 410 and 310 are provided with caps 700 that have the same structure for covering the exposed surfaces of the probe bodies, respectively.

Meanwhile, the caps 700 may have different colors so that the functions of the caps are identified.

Each of the detection and light-emitting probe bodies 410 and 310 is provided with a main protrusion 412 on the side facing the subject, and an optical fiber 413 that connects the tip of the main protrusion 412 and the detection unit 411 or the light emitting unit 311. The structure where a plurality of sub-protrusions 414 are disposed around the main protrusion 412 is employed in this embodiment. Further, the light-emitting probe 300 also includes a main protrusion 412 that is provided with a radiation optical fiber 413 on a contact surface 60 coming in contact with a subject 50, and employs the structure of "surface contact composed of a plurality of points" where a plurality of sub-protrusions 414 are disposed around the main protrusion 412.

Furthermore, the detection and light-emitting probe bodies 410 and 310 are rotatably mounted about the main protrusion 412 on the detection probe mounting part 450 and the light-emitting probe mounting part 350, respectively. According to the plurality of sub-protrusions 414 and the rotational structure, it is possible to ensure a function of pushing aside subject's hair and to control the posture of the probe.

One significant characteristic of the probe device of this embodiment is that the periphery of the sheet-like probe holder 200 is held, a predetermined interval is maintained between the probe holder 200 and a subject's scalp, and a sheet holding unit 500 for ensuring a light-shielded space 501 where light is shielded by the probe holder 200 and the subject's scalp is employed. According to the embodiment in which the light-shielded space 501 is formed, a space large enough to change the postures of the detection and light-emitting probe bodies 410 and 310 and to ensure breathability for sweating are ensured. In addition, since the sheet holding unit 500 is made of a soft material such as rubber, the subject easily puts on the probe device.

Further, the sheet holding unit 500 includes a differential amplifier, an A/D converter, and a probe communication part in electronic substrate arrangements 502 disposed on both sides. Accordingly, if the probe device is mounted on the subject, the subject can be in a standby state, so that correspondence can be improved.

An inspection device according to this embodiment will further be described below with reference to FIGS. 2 to 12B. Meanwhile, the same portions or arrows are indicated by the same reference numerals. The description to be repeated will be omitted.

Figure 2:
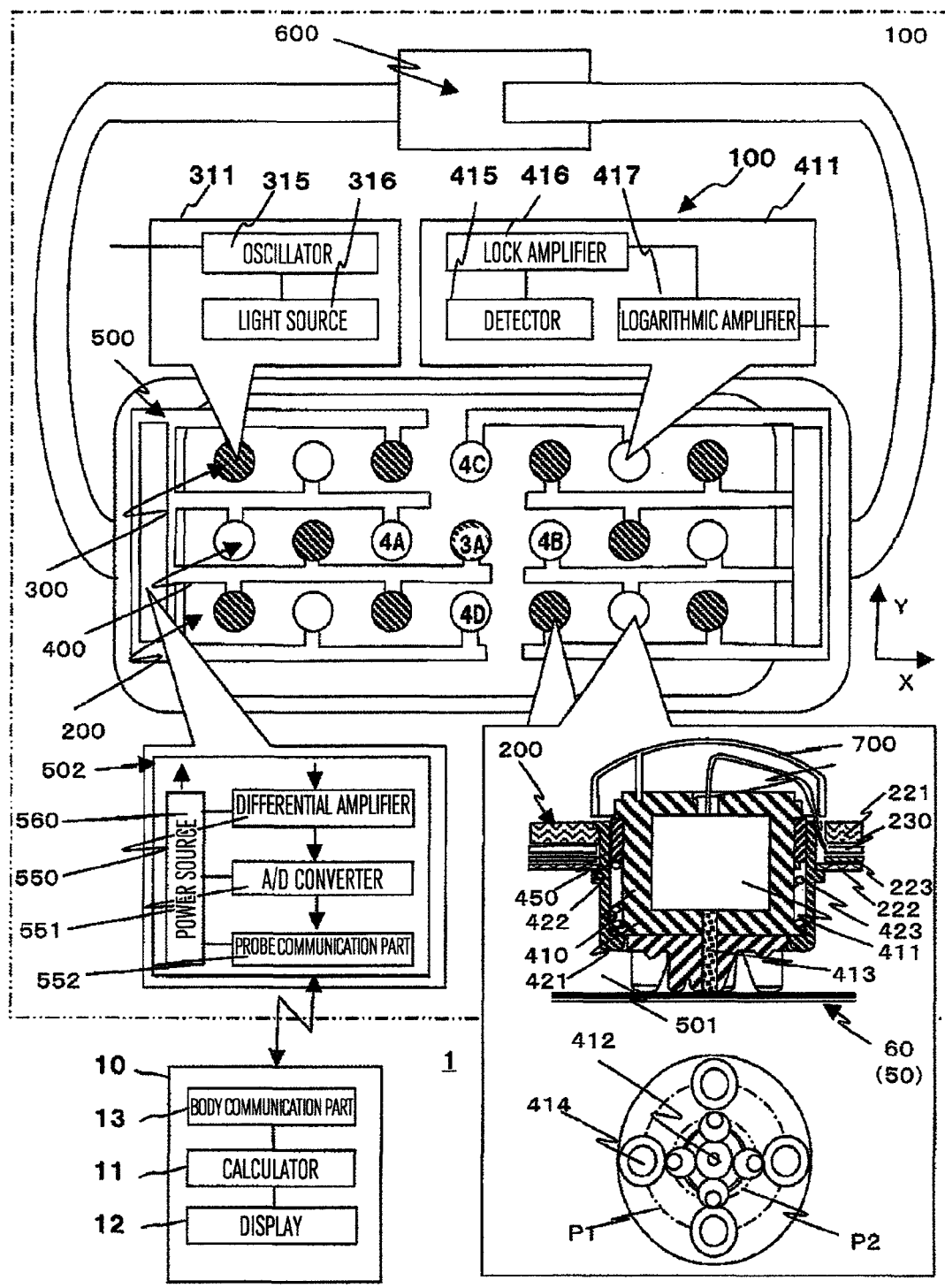
FIG. 2 is a view showing a schematic structure of a biological light measuring apparatus according to the embodiment shown in FIG. 1.

First, the schematic structure of the biological light measuring apparatus according to the first embodiment will be described with reference to FIG. 2. FIG. 2 is a view showing the schematic structure of the biological light measuring apparatus according to this embodiment.

In FIG. 2, the biological light measuring apparatus, which is generally indicated by reference numeral 1, includes a probe device 100 that is mounted on a head of the subject, and a biological light measuring apparatus body 10 that performs image processing of an electric signal output from the probe device 100 and displays the electric signal on a map. As described above, the probe device 100 includes the probe holder 200, the plurality of light-emitting probes 300 and the plurality of detection probes 400, the sheet holding unit 500, the fixing band 600, the caps 700 and so on.

The probe holder 200 is formed in a substantially horizontally long rectangular shape, the periphery of the probe holder 200 is surrounded by the thick (deep) sheet holding unit 500, and the fixing band 600 is attached to both ends of the sheet holding unit 500 in a longitudinal direction, so that the probe device 100 according to this embodiment has an appearance of a "goggle shape". Further, according to this embodiment, a portion of the probe holder 200 in the longitudinal direction is set to be pressed against the head of the subject in a direction where the posture of the head of the subject becomes horizontal. At this posture, the probe holder 200 is set to a predetermined position of the head of the subject at a predetermined interval with the sheet holding unit 500 interposed therebetween and further is set to ensure the light-shielded space 501 where light is shielded. In addition, since being made of a flexible material, the sheet holding unit 500 may be formed in a curved shape corresponding to the spherical shape of the head of the subject. Therefore, it is possible to fit the probe holder 200 to the head of the subject. Further, since the fixing band 600 has existing structure of which the length can be adjusted, the probe device 100 can be set at a predetermined position of the head of the subject so as to correspond to the subject's figure.

Furthermore, the sheet holding unit 500 is provided with the electronic substrate arrangements 502 on both sides in the longitudinal direction thereof. That is, as shown in a balloon at a lower left portion of FIG. 2, the sheet holding unit includes the differential amplifier 550, the A/D converter 551, the probe communication part 552, and a power source 560. In this embodiment, wiring sheets 230 are employed as one of the laminated members of the probe holder 200. The wiring sheets 230 are composed of a plurality of strip-shaped sheets that are wired so as to be laid between the light-emitting probes 300 and the detection probes 400 that are arranged in a matrix. In this embodiment, the wiring sheets 230 have a pair of divided left and right structures, and the light-emitting probes 300 and the detection probes 400, which are to be connected to the wiring sheets, are wired on the electronic substrate arrangements 502 that are disposed on both sides.

Meanwhile, in this embodiment, the light-emitting probes 300 and the detection probes 400 arranged in matrix have been divided into left and right portions, and been wired on the left and right electronic substrate arrangements 502 by a pair of left and right wiring sheets 230. However, the invention is not limited thereto. For example, the light-emitting probes 300 and the detection probes 400 may be divided and wired on left and right sides, the light-emitting probes and the detection probes may be wired on left and right sides for each line, or may be wired on one electronic substrate arrangement 502 provided on one side.

In addition, the electronic substrate arrangements 502 have been provided in the sheet holding unit 500 in this embodiment. However, the electronic substrate arrangements 502 may be provided on a separate holder substrate that is connected to the probe device through a cord.

Meanwhile, the plurality of light-emitting probes 300 and the detection probes 400 are alternately disposed in a matrix so that the detection probes 400 are positioned on both sides of the light-emitting probe 300. Accordingly, light radiated from one light-emitting probe 3A can be detected by the detection unit 411 composed of four detection probes 4A, 4B, 4C, and 4D that are disposed adjacent in X- and Y-directions. In other words, one detection probe 400 can detect light radiated from four light-emitting probes 300 that are disposed adjacent in the X- and Y-directions. That is, according to this embodiment, it is possible to measure the change of a dynamic state of blood over the entire region on which the probe device 100 is mounted.

Further, as shown in a balloon at a lower right portion of FIG. 2, the light-emitting probe 300 and the detection probe 400 have the same structure. The structure of the detection probe 400 will be mainly described herein, and a difference between the detection probe 400 and the light-emitting probe will be mainly described for the light-emitting probe 300.

The light emitting unit 311 includes a light source 315 that is shown in a balloon at an upper left portion of FIG. 2, and an oscillator 316 that removes noises generated from the outside. In this case, a semiconductor laser, a titanium-sapphire laser, a light-emitting diode, or the like may be used as the light emitting unit 311. The light-emitting probe body 310, which employs the light emitting unit 311 provided with a light-emitting diode, will be described in this embodiment.

Further, the detection unit 411 includes a detector 415 that is shown in a balloon at an upper right portion of FIG. 2, a lock amplifier 416, and a logarithmic amplifier 417. In this case, a photoelectric transducer, such as a photodiode and a photomultiplier tube, may be used as the detection unit 411. The detection probe body 410, which employs the detection unit 411 provided with a photodiode, will be described in this embodiment.

Meanwhile, the biological light measuring apparatus body 10 includes a calculator 11, a display 12, and a body communication part 13. In this embodiment, the biological light measuring apparatus body 10 and the probe device 100 are provided with the body communication part 13 and the probe communication part 552, respectively, so that the biological light measuring apparatus body 10 and the probe device 100 can be electrically and cordlessly connected to each other. For this reason, a subject on which the probe device 100 is mounted at the head is electrically connected to the biological light measuring apparatus body 10 without being connected by a cord. Therefore, the inspection result of the subject can be measured by the biological light measuring apparatus body 10 without the restriction that is caused by cords.

According to the biological light measuring apparatus 1, the weak near infrared light (light) of about 1.5 mW, which is radiated from the light source 315 receiving power from the power source 560 of the electronic substrate arrangements 502, is condensed in the light source 315 by a lens system (not shown), and is radiated to the head of the subject 50 through the radiation optical fiber 413 of the protrusion 412 that is provided below the light source 315. The light emitted from the light source 315 is intensity-modulated into light, which has frequency f in the range of about 100 Hz to 10 MHz, by the oscillator 316 in order to remove the noises generated from the outside.

The wavelength of the used light depends on the spectral characteristics of noticed substance in a living body. However, when the oxygen saturation or the amount of blood is measured from the concentration of Hb and Hb02 in blood, light having one or more wavelengths is selected from light having wavelength in the range of 600 to 1400 nm. The light, which is radiated to the head of the subject 50, passes through the visual region of the radiation optical fiber 413, passes through a region where the dynamic state of blood is locally changed in blood vessels of the visual region, and is detected by the detector 415 through the detection optical fiber 413 of the protrusion 412 that is provided below the detection unit 411.

The light, which is detected by the detection unit 411 through the detection optical fiber 413, is photoelectrically converted by the detection unit 411, and the intensity of the passing-through light is output in the form of the intensity of an electric signal. Light intensity-modulated frequency components of the light source are extracted by the lock amplifiers 416 thereof, from the electric signals, which represent the intensities of the passing-through light output from the plurality of detection units 411, are logarithmically converted by the logarithmic amplifiers 417 of the detection units, and then are collected by the electronic substrate arrangements 502 through the wiring sheets 230.

The signals collected by the plurality of detection units 411 are input to the differential amplifier 550 of the electronic substrate arrangements 502. In the differential amplifier 550, for example, the output from a detection probe 400*a* is input to a negative electrode and the output from a detection probe 400*b* is input to a positive electrode. As a result, a differential signal of the intensities of the passing-through light at two different positions is output as an output signal. The output signal output from the differential amplifier 550 is converted into a digital signal by the A/D converter 551, and then is transmitted to the biological light measuring apparatus body 10 through the probe communication part 552.

The signal, which is received in the biological light measuring apparatus body 10 through the body communication part 13, is input to the calculator 11 and processed by the calculator. Then, the signal is displayed on the display 12 as time series data. In this embodiment, the wireless communication type has been employed as the communication means between the body communication part 13 and the probe communication part 552, but the communication means may be parts that transmit and receive signals through infrared or other communication units. Of course, the parts may be connected by cords. However, the subject's degree of freedom in action is restricted in this case.

Further, in this embodiment, as shown in the balloon at the lower right portion of FIG. 2, the sheet-like probe holder 200 includes an outer sheet 221 that is provided on the outer surface of the probe holder 200, an inner sheet 222 that is provided on the inner surface of the probe holder 200 facing the head of the subject, and a light-shielding sheet 223 and a wiring sheet 230 that are provided between the outer and inner sheets 221 and 222. In this embodiment, each of the outer and inner sheets 221 and 222 is formed of a cubic fabric that is made of a resin fiber having a thickness in the range of 5 to 10 mm.

The cubic fabric is generally called a three-dimensional fabric, and is a fabric that is obtained by sterically weaving (filamentous) fibrous materials in three directions of vertical, horizontal, and perpendicular directions. Any material, that is, a polyester fiber that is manufactured using polyethylene terephthalate, polybutylene terephthalate, and poly trimethylene terephthalate; cotton; a cellulose fiber, such as cupra rayon, viscose rayon, and a purified cellulose fiber; and a polyamide fiber manufactured using nylon6 or nylon66 may be used as the material of a connecting strand. As for the form of the fiber, any fiber, such a filament yarn or a span yarn, may be employed.

Since the cubic fabric is employed in this embodiment, it is possible to form the light-emitting probe mounting part 350 or the detection probe mounting part 450 at an appropriate thickness, to reduce the weight of the probe mounting parts, to reliably hold the probe mounting parts, and to allow a subject to sweat well through spaces formed in the fabric.

Meanwhile, the light-shielding sheet 223 is to improve the light-shielding property of a probe holding part 220 that is made of a cubic fabric. In this embodiment, a fabric made of a black resin fiber is inserted between the outer sheet 221 and the inner sheet 222. If the light-shielding sheet 223 is employed, it is possible to prevent external light from entering the probe holding part 220, and to also absorb reflected light reflected from the scalp. Therefore, it is possible to also expect an effect of improving measurement performance.

A strip-shaped flexible printed circuit board, where copper foil is attached to the surface of, for example, the thin resin film, has been employed as the wiring sheet 230 in this embodiment. Accordingly, it is possible to obtain laminate structure on which wiring is performed without thickness deviation of the probe holding part 220.

Further, in this embodiment, the probe holder 200 is formed in a three-dimensional shape, which is curved so as to correspond to the curved shape of the head of the subject, by thermal compression bonding.

Furthermore, the structure of the "surface contact composed of a plurality of points" where the plurality of sub-protrusions 414 is disposed around the main protrusion 412 of the detection probe body 410 has been employed in this embodiment.

The light-emitting probe or the detection probe in the related art employs a method of "point contact using one point" where the radiation or detection optical fiber is directly reinforced or reinforced by a protrusion on the contact surface 60 coming in contact with the subject 50. For this reason, there is the following problem: it is difficult to maintain the tip of the optical fiber, which is provided to protrude from the tip of each of the plurality of probe bodies mounted on the probe holder, in the posture perpendicular to the scalp. A fine adjustment knob is provided to change the posture of the tip of the optical fiber in the related art, but there is a problem that it takes long time to adjust the perpendicular postures of many probes.

In this embodiment, the contact with the biological surface (contact surface 60) of the subject 50 is performed by the structure that includes the main protrusion 412 and the plurality of sub-protrusions 414. The main protrusion is provided with the light transmission unit (the radiation optical fiber 313 or the detection optical fiber 413) communicating the light radiation unit (light emitting unit 311) or the light detection unit (detection unit 411) and the outside, at the axial center thereof. The plurality of sub-protrusions protrudes around the main protrusion 412 and has substantially the same length. Therefore, it is possible to easily support the light transmission unit in the posture perpendicular to the biological surface.

In this embodiment, as shown in the balloon at the lower right portion of FIG. 2, four sub-protrusions 414 are provided at regular intervals on each of the concentric circles P1 and P2 of the main protrusion 412, so that it is possible to suppress inclination in four directions. As a result, it is possible to reduce the problems of the related art.

Particularly, in this embodiment, a distance between the probe holder 200 and the biological surface (contact surface 60) is increased and the length of a portion of the probe holder 200, which protrudes upward, is reduced by the sheet holding unit 500. Therefore, each of the light-emitting probes 300 and the detection probes 400, which is held by the probe holder 200, has difficulty in making the tip of the main protrusion 412 come in contact with the biological surface (contact surface 60). In this respect, it is possible to suppress the inclination of the probe in four directions by the sub-protrusions 414. As a result, it is possible to solve the above-mentioned problems.

Meanwhile, if three or more sub-protrusions 414 are provided around the main protrusion 412, the detection probe body 410 including the sub-protrusions 414 stands by itself in the perpendicular posture. Therefore, it is possible to expect the same effect as described above.

Further, in this embodiment, if the sub-protrusion 414 is made of a slightly soft material such as a resin material, rubber, or elastomer that has flexibility, it is possible to form a sub-protrusion friendly to the subject 50 and to easily make the detection probe body 410 be in the perpendicular posture.

Since the light-emitting probe 300 also has the same structure as described above, it is possible to expect the same effect as described above.

In this embodiment, the main protrusion 412 and the plurality of sub-protrusions 414 are supported rotatably about the main protrusion 412. This kind of the biological light measuring apparatus has a problem in that the tip of the optical fiber does not come in contact with the biological surface of the subject 50 due to the hair on the biological surface. However, in the related art, a contact point between the probe and the scalp forms "one point contact". Accordingly, there is a problem in that it takes long time to adjust the perpendicular postures of many probes while pushing aside the hair in order to push aside the hair and perform adjustment at the tip of the optical fiber.

In this embodiment, the light-emitting probe body 310 and the detection probe body 410, which include the main protrusion 412 and the sub-protrusions 414, are supported rotatably about the main protrusion 412. Therefore, when the sub-protrusions 414 rotate, the tips of the sub-protrusions 414 push aside the hair, so that the tip of the detection optical fiber 413 easily comes in close contact with the biological surface. In addition, the sub-protrusions 414 rotate about the main protrusion 412, so that the detection probe body 410 can be easily in the perpendicular posture.

Further, the sub-protrusion 414 is made of a flexible material, and the detection optical fiber 413 is provided at the axial center and the flexible sub-protrusions 414 rotate about the main protrusion 412 having strength higher than the sub-protrusion 414. Accordingly, it is possible to easily push aside the hair and control the posture. In addition, since two-stage sub-protrusions 414 are provided around the main protrusion 412 in this embodiment, it is possible to push aside the hair even though the sub-protrusions rotate in a small rotation range.

Meanwhile, since the light-emitting probe 300 also has the same structure as described above, it is possible to expect the same effect as described above.

Furthermore, in this embodiment, the light-emitting probe body 310 and the detection probe body 410 are exposed to the outer surface of the probe holder 200 and the caps 700 are mounted on the exposed portions thereof, so that it is possible to rotate the light-emitting probe body 310 and the detection probe body 410 by the caps 700. For this reason, even while the subject puts on the probe device 100, it is possible to grasp the caps 700 exposed to the outer surface of the probe holder 200 with fingers and to rotate the caps. Accordingly, it is possible to easily rotate the sub-protrusions 414. As a result, it is possible to easily push aside the hair and to change the posture of the probe.

Signal connectors 418 are provided at the portions of the light-emitting probe body 310 and the detection probe body 410 that are covered with the caps 700. Accordingly, wiring connection is easily performed by attaching or detaching the caps 700. In addition, since the wiring connection is not affected by the rotation of the light-emitting probe body 310 and the detection probe body 410, disconnection of the wiring does hardly occur. Further, since the wiring connected portions are shielded by the caps 700, the connected portions are not dropped out and the appearance is improved.

In this embodiment, the light-emitting probe body 310 or the detection probe body 410 includes a first casing 421 that is provided with the light emitting unit 311 or the detection unit 411, and a second casing 422 that is rotatably mounted around the first casing 421. The first casing 421 is provided with the main protrusion 412 and the sub-protrusions 414, and the second casing 422 is detachably mounted on the light-emitting probe mounting part 350 or the detection probe mounting part 450.

According to this structure, it is possible to rotate the first casing 421 that includes the main protrusion 412 and the sub-protrusions 414, and to attach/detach the detection probe body 410, which includes the first casing 421 and the second casing 422, to/from the detection probe mounting part 450.

Further, since being provided with a spring 423, the second casing 422 can make the first casing 421 slide toward the subject by the spring 423. Accordingly, it is possible to improve the degree of adhesion of the surface contact composed of a plurality of point contacts correspondingly to the concavity and convexity of the head of the subject.

Figure 3:
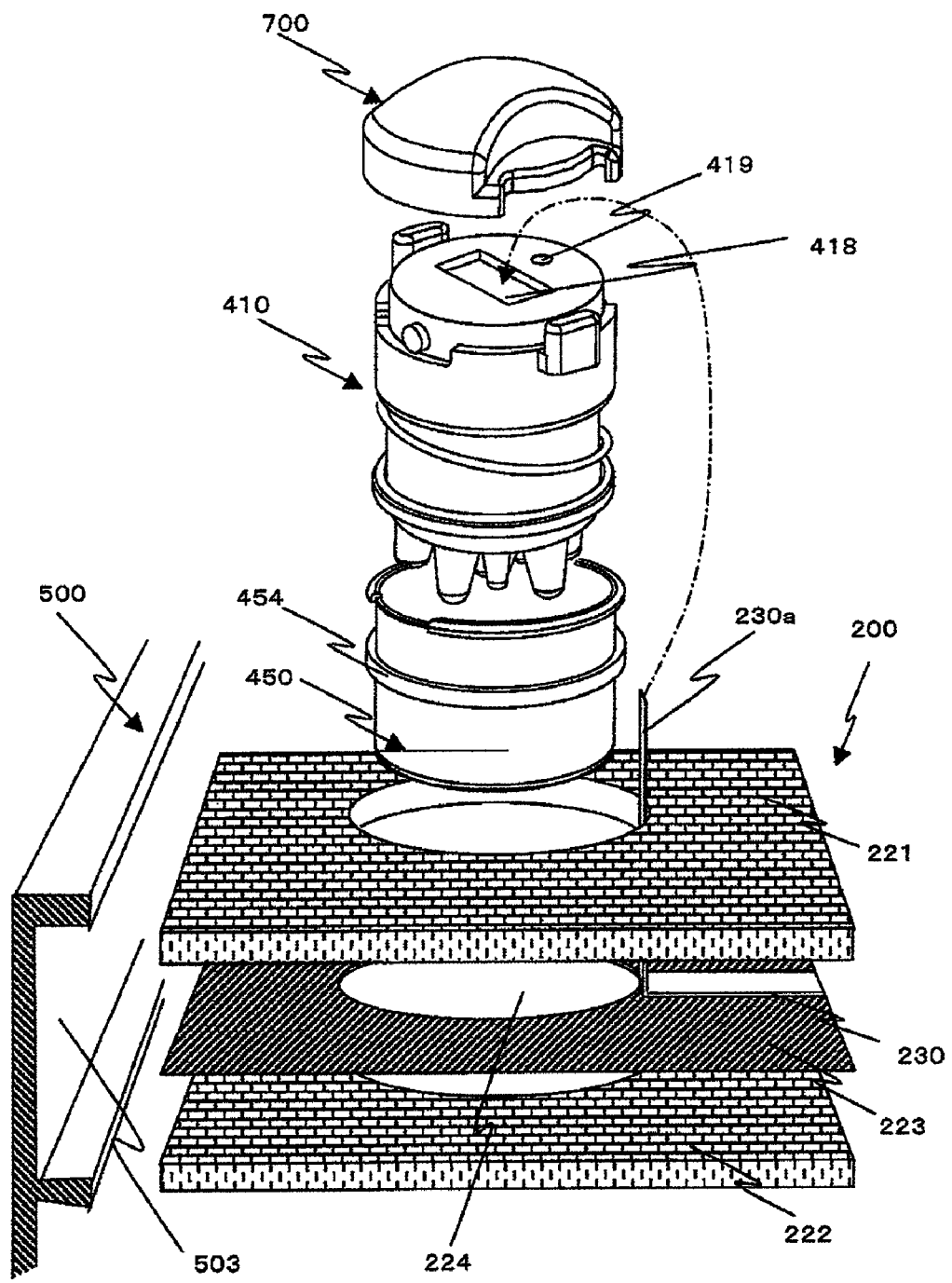
FIG. 3 is a development view of a peripheral structure of a detection probe.
Figure 4:
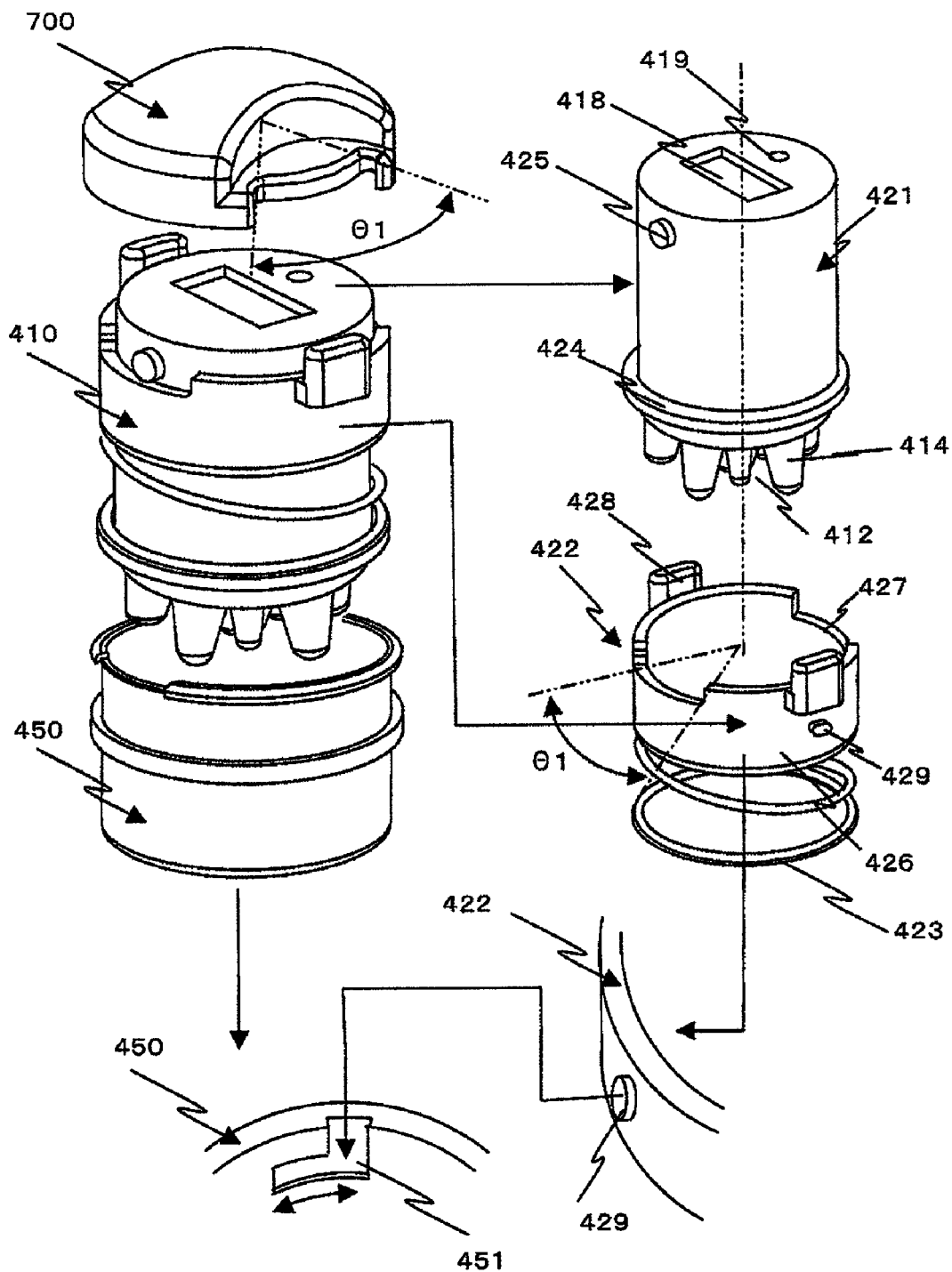
FIG. 4 is a development view of the peripheral structure of the detection probe.
Figure 5:
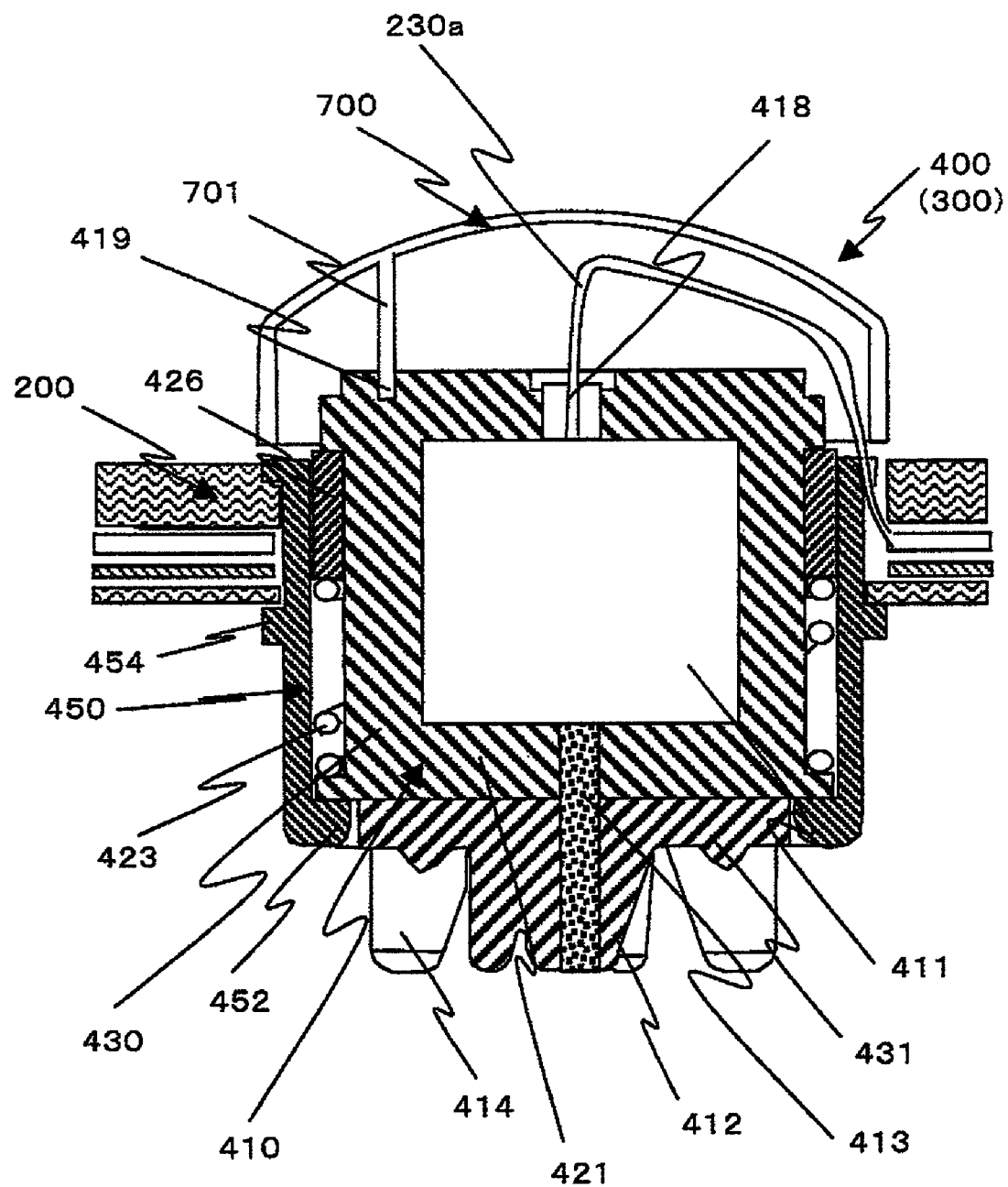
FIG. 5 is a cross-sectional view of the detection probe.
Figure 6A:
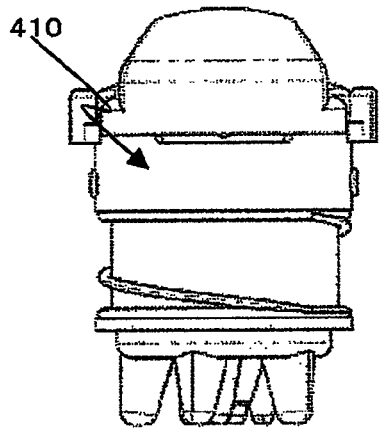
FIGS. 6A to 6F are external views of the detection probe.
Figure 6B:
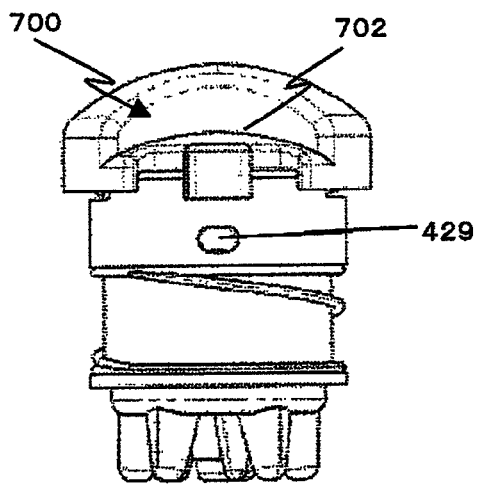
Figure 6C:
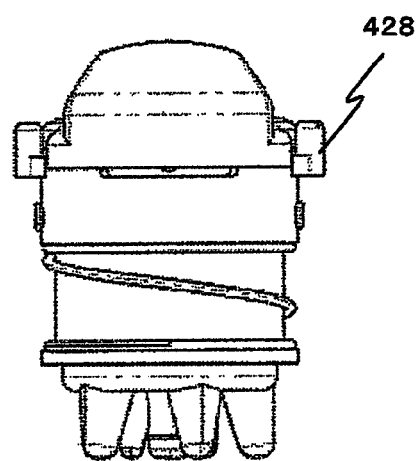
Figure 6D:
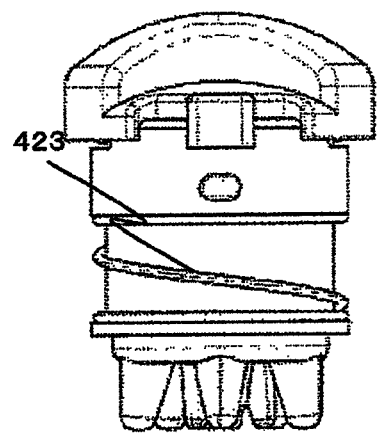
Figure 6E:
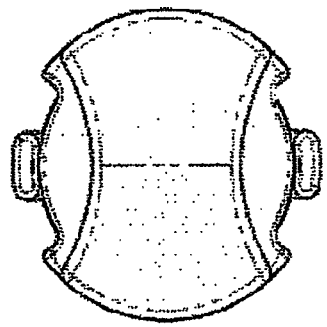
Figure 6F:
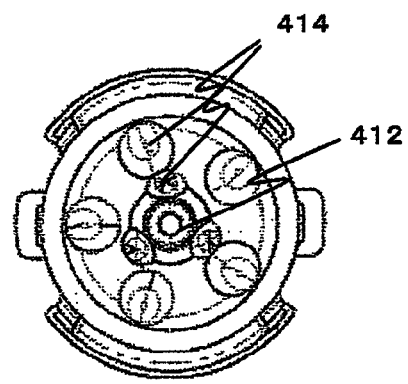
Figure 7A:
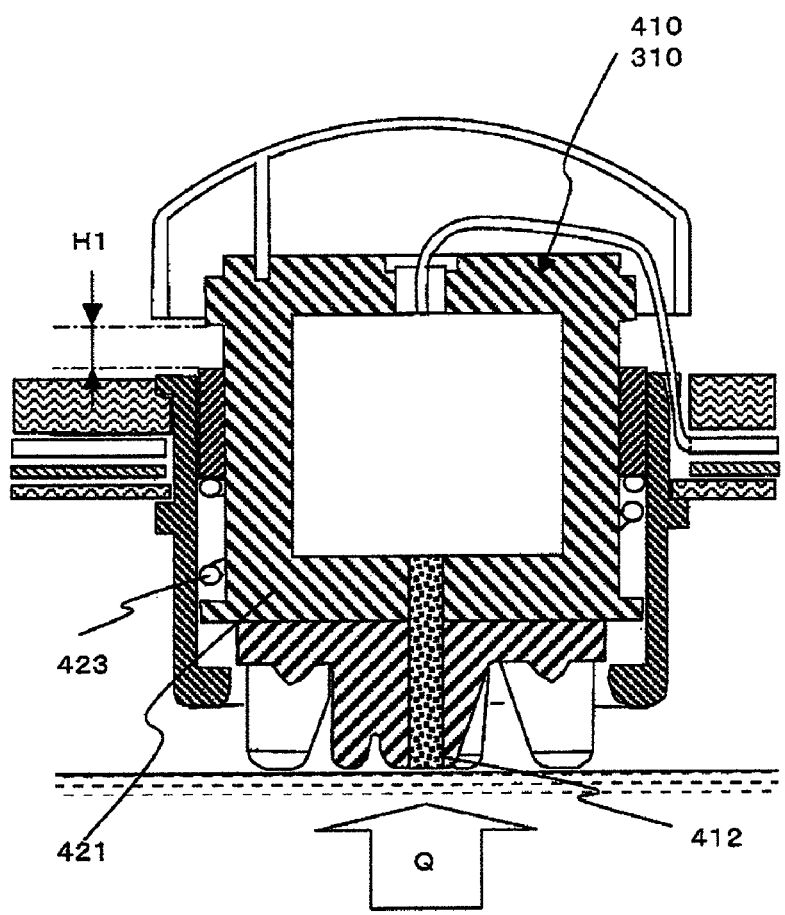
FIGS. 7A to 7C are views illustrating an extension-contraction mechanism of the detection probe.
Figure 7B:
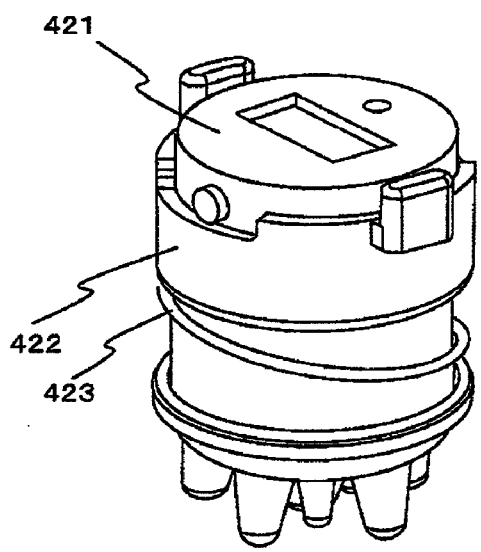
Figure 7C:
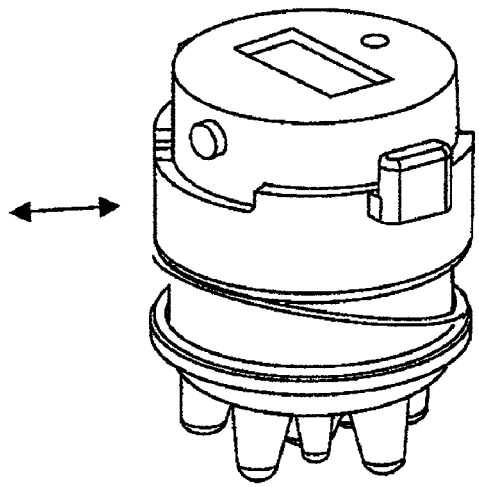
Figure 8A:
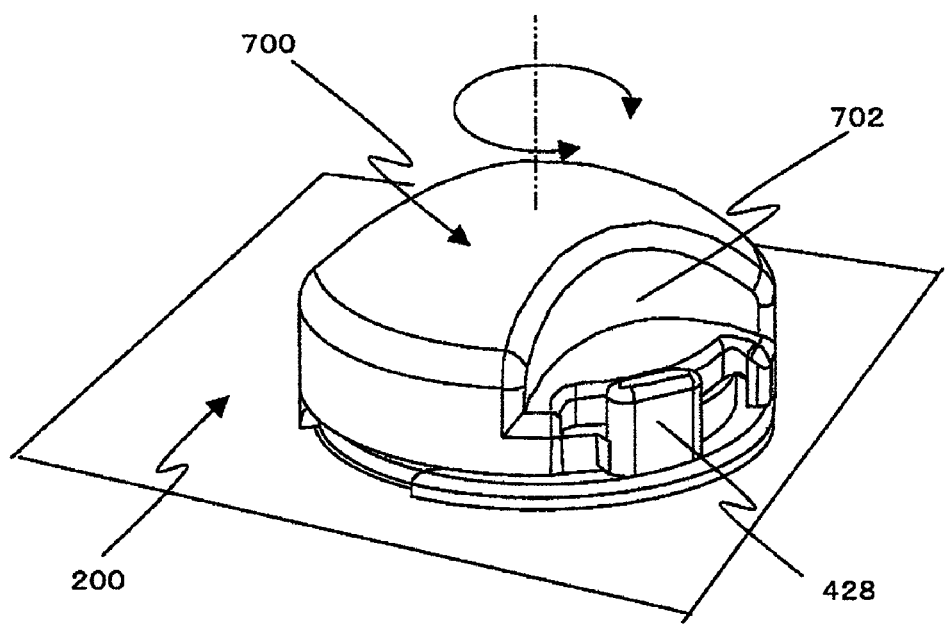
FIGS. 8A and 8B are views illustrating the rotation of the detection probe.
Figure 8B:
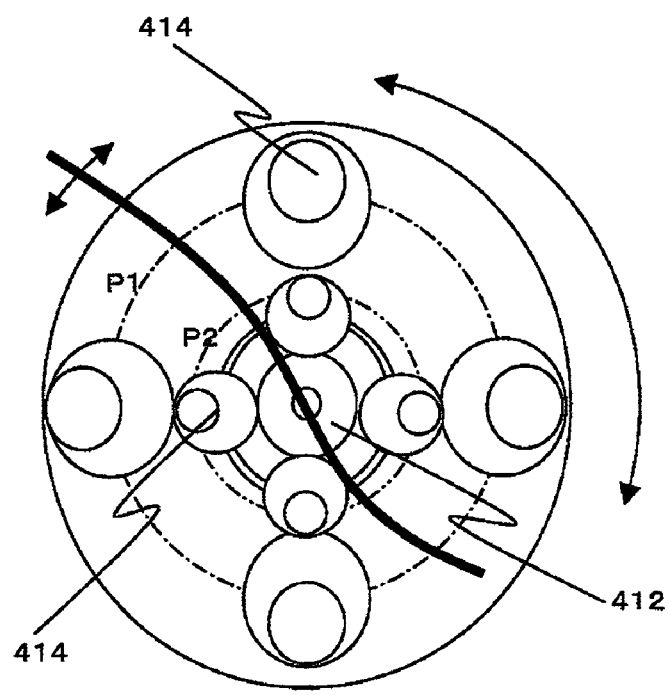

Next, the peripheral structure of the detection probe according to the embodiment of the invention will be described in more detail below with reference to FIGS. 3 to 8. FIG. 3 is a development view of the peripheral structure of the detection probe. FIG. 4 is a development view of the peripheral structure of the detection probe. FIG. 5 is a cross-sectional view of the detection probe. FIGS. 6A to 6F are external views of the detection probe: FIG. 6A is a front view, FIG. 6B is a right side view, FIG. 6C is a rear view, FIG. 6D is a left side view, FIG. 6E is a plan view, and FIG. 6F is a bottom view. FIGS. 7A to 7C are views illustrating an extension-contraction mechanism of the detection probe: FIG. 7A is a cross-sectional view, FIG. 7B is a perspective view of the extended extension-contraction mechanism, and FIG. 7C is a perspective view of the contracted extension-contraction mechanism. FIGS. 8A and 8B are views illustrating the rotating state of the detection probe: FIG. 8A is an external perspective view, and FIG. 8B is a bottom view. In this case, since the light-emitting probe 300 has the same structure as the detection probe 400 as described above, the description thereof will be omitted herein.

In FIG. 3, a plurality of openings 224 to which the detection probe mounting parts 450 are mounted are formed in the probe holder 200 at a predetermined position. Further, the probe holder 200 has the laminate structure where the light-shielding sheet 223 and the wiring sheet 230 are provided between the outer sheet 221 and the inner sheet 222. In this embodiment, the wiring sheet 230 is provided close to the outer sheet 221, and the light-shielding sheet 223 is provided close to the inner sheet 222.

In this embodiment, the detection probe mounting part 450 has a cylindrical appearance of which the height is small, and includes a pair of ring-shaped flanges 454, which protrudes from the outer periphery of the detection probe mounting part, at one end thereof. The opening 224 is fitted between the pair of flanges 454, so that the detection probe mounting part is fixed to the probe holder.

In this embodiment, when assembling is performed, there are prepared the outer sheet 221, the inner sheet 222, and the light-shielding sheet 223, through which openings 224 are previously formed. Then, the wiring sheet 230 is bonded to the sheets in a predetermined order, while positioning them at the openings 224, by thermal compression bonding. When the wiring sheet is bonded to the sheets, thermal compression bonding is performed so that a connection terminal 230a of the wiring sheet 230 is exposed through the opening 224, which makes the wiring sheet be easily connected to the detection probe 400 later.

The probe holder 200 of which the periphery is cut into a predetermined size is inserted into a bonding groove 503 of which the peripheral end is formed on the inner surface of the sheet holding unit 500, and is fixed to the bonding groove by an adhesive or the like. When the probe holder is fixed to the bonding groove, the other end of the wiring sheet 230 is bonded to the electronic substrate arrangements 502.

Meanwhile, the detection probe body 410 (the light-emitting probe body 310) is detachably mounted on the detection probe mounting part 450 (the light-emitting probe mounting part 350) that is fixed to the probe holder 200 at a predetermined position. Further, the connection terminal 230a of the wiring sheet 230 is connected to the signal connector 418 formed at the upper portion of the detection probe body 410 that is mounted on the detection probe mounting part 450.

Furthermore, a cap mounting hole 419 is formed adjacent to the signal connector 418 at the upper portion of the detection probe body 410. A connecting rod 701 (see FIG. 5) formed in the cap 700 is inserted into the cap mounting hole 419, so that it is possible to mount the cap 700.

Next, the detailed structure of the detection probe body 410 and the mounting structure of the detection probe mounting part 450 therewith will be described below with reference to FIGS. 4 to 8B. In FIG. 4, the detection probe body 410 includes a cylindrical first casing 421 and a second casing 422 disposed around the first casing.

In FIG. 4, the signal connector 418 and the cap mounting hole 419 are formed on the upper surface of the first casing 421, and the main protrusion 412 and the plurality of sub-protrusions 414 are formed on the lower surface of the first casing. Further, a flange 424 is provided to protrude outward from the lower end portion of the peripheral side surface of the first casing, and a pair of protrusions 425 are formed at opposite positions of the upper end portion on the peripheral side surface of the first casing.

Meanwhile, the second casing 422 includes a cylindrical outer casing 426 and a coiled spring body 423. Recesses 427 are formed to be recessed at opposite positions on the upper end of the outer casing 426, and grip parts 428 are formed to protrude upward (in an axial direction) and outward from the upper end of the outer casing at positions deviated from the recesses 427 by an angle of 90°. The grip parts 428 may be used as finger tabs that are used to attach/detach the detection probe body 410 to/from the detection probe mounting part 450.

Further, the first casing 421 and the second casing 422 are assembled as follows: the spring body 423 is fitted on the outer periphery of the first casing 421, and the outer casing 426 is then fitted on the outer periphery of the first casing, so that the spring body 423 and the outer casing 426 are caught and held between the flange 424 and the protrusions 425. With this structure, one end of the spring body 423 is fixed to the flange 424, and the other end thereof presses the outer casing 426 against the protrusions 425. Meanwhile, the outer casing 426 is arrested at one end side by the protrusions 425 and cannot be moved. However, since the spring body 423 is extended and contracted, the first casing 421 can slide at the other end side of the outer casing.

Further, a pair of fixing protrusions 429 are formed at opposite positions on the outer periphery of the outer casing 426. Meanwhile, L-shaped coupling grooves 451, each of which extends downward from an upper end of the detection probe mounting part 450 and then extends transversely, are formed on the inner surface of the detection probe mounting part 450. With this structure, the assembled detection probe body 410 is inserted into the detection probe mounting part 450 so as to fit the fixing protrusions 429 of the outer casing 426 into the coupling grooves 451 of the detection probe mounting part 450. Then, by rotating the detection probe body, it is possible to fix the detection probe body 410 to the detection probe mounting part 450.

In this way, the detection probe body 410 can be easily attached to and detached from the detection probe mounting part 450 in this embodiment. Therefore, it is possible to easily perform the maintenance of the detection probe body 410.

Further, in this embodiment, the protrusions 425 formed on the peripheral side surface of the first casing 421 are fitted in the recesses 427 of the outer casing 426, and the protrusions 425 are moved in the recesses 427 in a circumferential direction of the outer casing, so that the first casing 421 can rotate the detection probe body 410. Accordingly, the detection probe body 410 can be rotated to swing in the circumferential direction in a range of an angle θ1 corresponding to the recess 427. The reason for this is as follows: a trouble occurs in the wiring connection between the signal connector 418 and the connection terminal 230a if the rotation range is not limited, and the operation of pushing aside the hair or the posture change of the detection probe body 410 can be sufficiently achieved by the swing operation.

In FIG. 5, a flange 452 is formed to protrude inward from the lower end on the inner surface of the cylindrical detection probe mounting part 450. The fixing between the detection probe mounting part 450 and the detection probe body 410 is performed by fixing the outer casing 426 to the detection probe mounting part 450. Accordingly, the lower end of the first casing 421, which slides with respect to the outer casing 426, is always pressed against the flange 452.

In contrast, when pressure Q is applied to the probe from the subject as shown in FIGS. 7A-7C, the probe is operated from a state where the spring body 423 is extended as shown in FIG. 7B to a state where the spring body 423 is contracted as shown in FIG. 7C. Accordingly, the first casing 421 moves upward as shown in FIG. 7A, so that the probe is operated to absorb the pressure Q applied from the subject. Therefore, each of the plurality of detection and light-emitting probe bodies 410 and 310 corresponds to the concavity and convexity of the head of the subject, so that the tips of the main protrusions 412 of the detection and light-emitting probe bodies 410 and 310 can come in close contact with the scalp of the subject. As a result, since each first casing 421 protrudes upward from the detection probe mounting part 450 by a distance H1 and absorbs the pressure Q, it is possible to fit the entire probe device 100 to the head of the subject.

Returning to FIG. 5, the first casing 421 is divided into a main casing 430 that includes the detection unit 411, and a cushion part 431 that includes the main protrusion 412 and the sub-protrusions 414. Since being made of a soft material, the cushion part 431 can come in contact with the scalp of the subject without pain. Further, since being attached to the main protrusion 412 by an adhesive, the cushion part 431 may be replaced as consumables.

Furthermore, as shown in FIGS. 6F and 8B, the sub-protrusion 414 is formed in an inverted truncated conical shape with a rounded summit, and is formed to be opened from the inner side toward the outer side. For this reason, the tips of the plurality of sub-protrusions 414 always come in close contact with the scalp of the subject. That is, it is possible to make the detection probe body 410 stand by itself on the scalp of the subject. The self-standing can be further achieved by rotating the detection probe body 410. Meanwhile, since considerably contributing to the control of the posture of the detection probe body 410 in this embodiment, the outer sub-protrusions 414 are formed to be thicker than the inner sub-protrusions 414. Further, the inner sub-protrusions 414 are to be buried between the outer sub-protrusions 414 and the main protrusion 412, and the main protrusion 412 and the sub-protrusions 414 form the structure of the "surface contact composed of a plurality of points". Accordingly, it is possible to make the detection probe body 410 stand by itself without giving the subject pain, to improve the efficiency of pushing aside the hair existing in the "surface contact" by rotating the sub-protrusions 414, and to make the tip of the main protrusion 412 come in close contact with the scalp.

Returning to FIG. 5, the cap 700 is formed to have a dome-shaped cross section, and the connecting rod 701 extends downward from the inner surface of the cap. Accordingly, when the cap 700 is grasped with fingers and rotated, the torque can make the sub-protrusions 414 of the first casing 421 be rotated by the connection between the connecting rod 701 and the cap mounting hole 419. Meanwhile, the connection terminal 230a is gotten in the cap 700, through the gap between the cap 700 and the detection probe body 410, and is connected to the signal connector 418.

Further, as shown in FIGS. 6A to 6F, the cap 700 includes cutout portions 702 on both sides thereof not to interfere with the pair of grip parts 428 formed on the second casing 422. As described with reference to FIG. 4, the cutout portion 702 is formed to have the same angle as the angle θ1 of the recess 427 of the second casing 422 in the circumferential direction. Furthermore, as shown in FIG. 8A, with the cutout portions 702 having the angle θ1, it is possible to make the pair of cutout portions 702 in a shape that is suitable to grasp the cap 700 with a thumb and an index finger.

Meanwhile, since the cutout portions 702 are formed in the cap 700, it is possible to easily grasp the pair of grip parts 428, which are disposed to fit into the cutout portions 702, with a thumb and an index finger. Therefore, it is possible to rotate the detection probe body 410, thereby simply attaching/detaching the detection probe body to/from the detection probe mounting part 450.

Figure 9A:
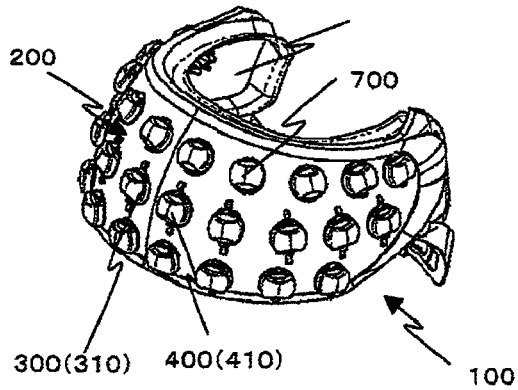
FIGS. 9A to 9F are external views of the probe device.
Figure 9B:
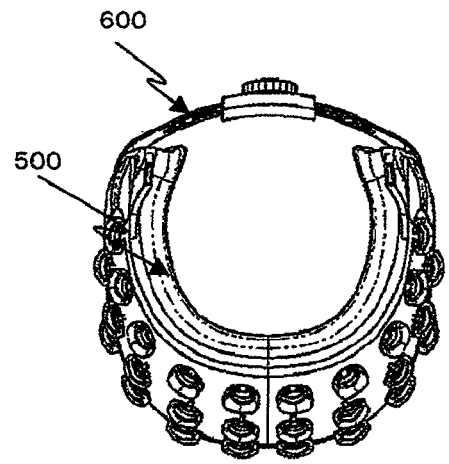
Figure 9C:
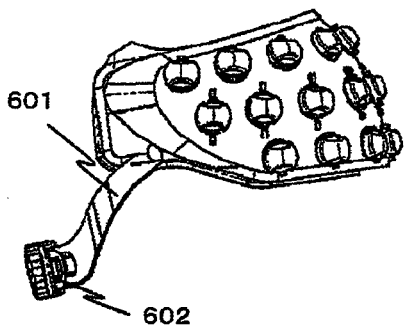
Figure 9D:
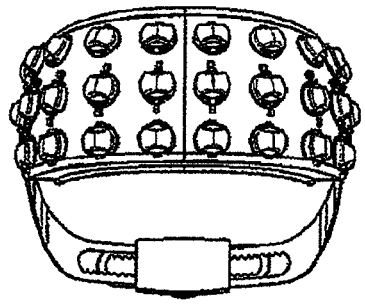
Figure 9E:
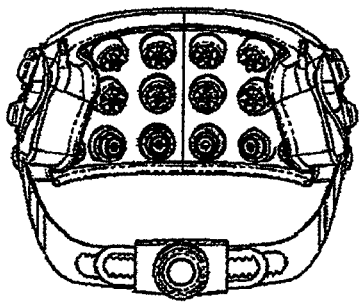
Figure 9F:
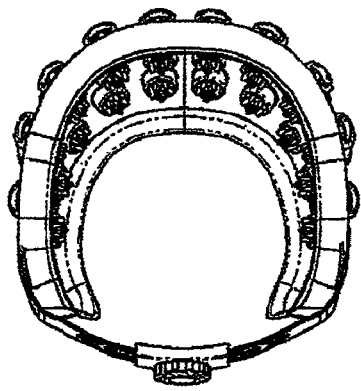
Figure 10A:
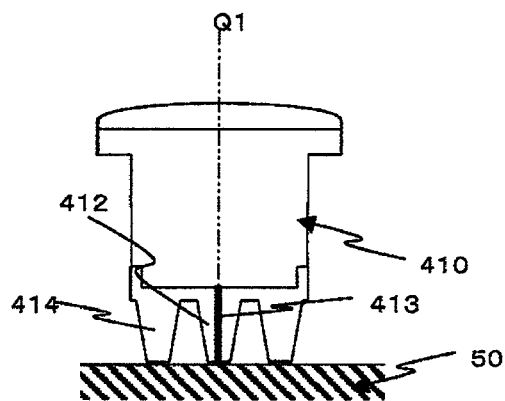
FIGS. 10A to 10C are views illustrating a vertical control operation of the detection probe.
Figure 10B:
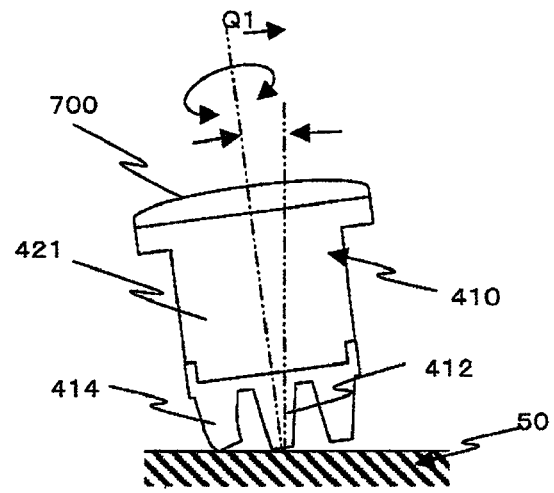
Figure 10C:
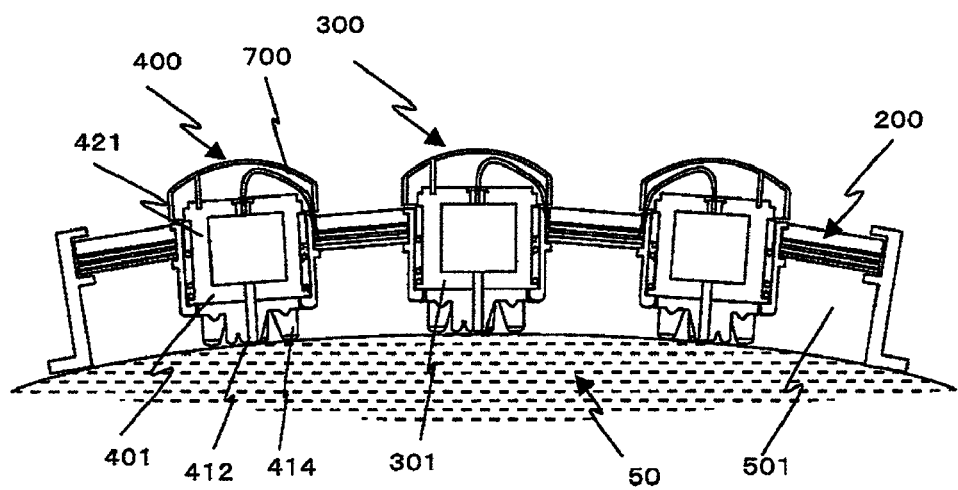
Figure 11A:
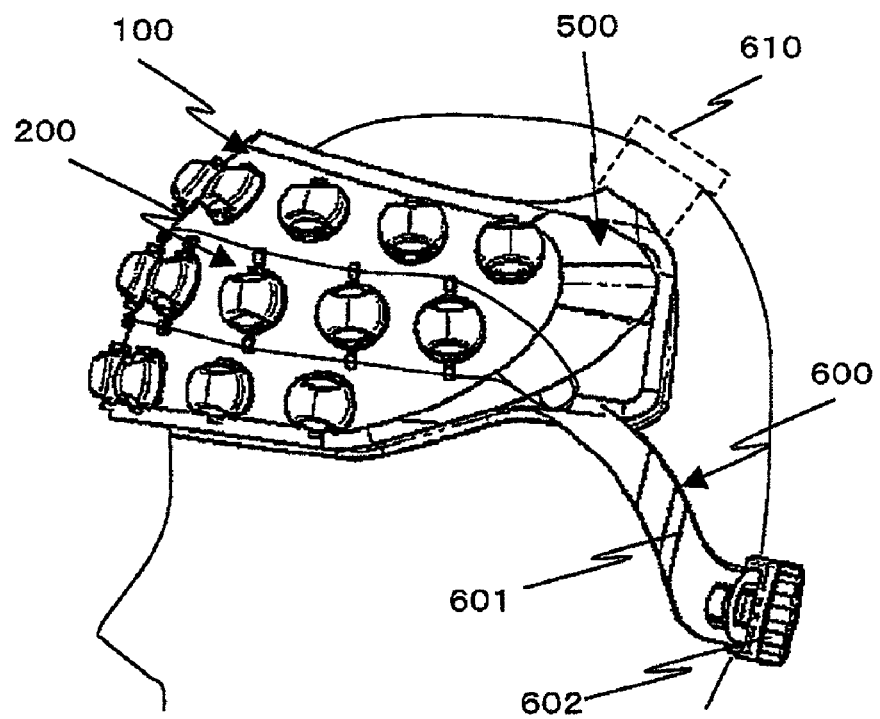
FIGS. 11A and 11B are views showing a head tightening structure of the probe device.
Figure 11B:
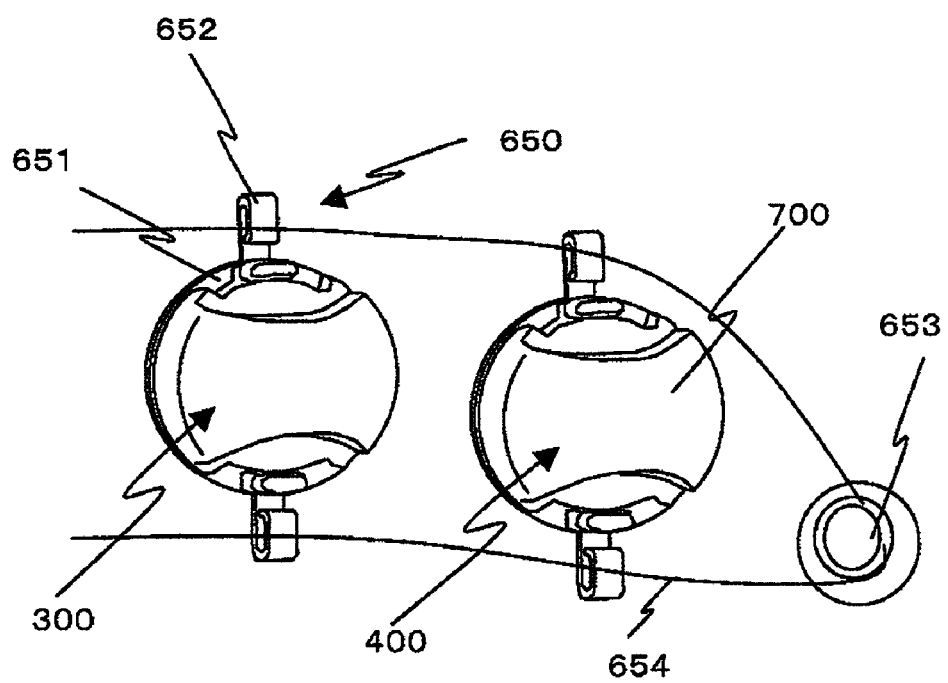

Next, the entire structure of the probe device 100 will be further described below with reference to FIGS. 9A to 11B. FIGS. 9A to 9F are external views of the probe device: FIG. 9A is a perspective view, FIG. 9B is a plan view, FIG. 9C is a left side view, FIG. 9D is a front view, FIG. 9E is a rear view, and FIG. 9F is a bottom view. FIGS. 10A to 10C are views illustrating a vertical control operation of the detection probe: FIG. 10A is a side view of the detection probe in a perpendicular posture, FIG. 10B is a view illustrating a posture control operation, and FIG. 10C is a cross-sectional view of the entire probe device. FIGS. 11A and 11B are views showing a head tightening structure of the probe device: FIG. 11A is a side view showing that the probe device is put on, and FIG. 11B is an enlarged view of the tightening structure.

First, referring to FIGS. 9A to 9F, in this embodiment, the probe holder 200 is formed in an oblong shape. The light-emitting probes 300 and the detection probes 400 are arranged in the area of the probe holder in a matrix that includes 10 columns and 3 lines. Further, in this embodiment, one of the light-emitting probes 300 or the detection probes 400, which are provided at a lower portion of the probe holder on both sides thereof, is removed, so that the both sides of the probe holder 200 is formed in a tapered shape. Furthermore, the periphery of the probe holder 200 having the oblong shape is held by the sheet holding unit 500. Since the sheet holding unit 500 is made of a soft material such as a rubber material and surrounds the periphery of the probe holder 200 in the form of a strip having thickness, a light-shielded space 501 having a uniform depth can be formed between the probe holder 200 and the head of the subject.

Both ends of the sheet holding unit 500 are also formed in a tapered shape, and one ends of belts 601 of the fixing band 600 can be attached to the tapered ends of the sheet holding unit. Belt fixing parts 602 of which ends are connected to each other and which adjust the length of the belts are provided at the other ends of the pair of belts 601. Therefore, the other ends of the pair of belts are pulled and fixed by the belt fixing parts 602, so that the sheet holding unit 500 can be fixed at an arbitrary position on the head. As a result, the subject can put on the probe device 100 like goggles.

As shown in FIG. 10C, the detection and light-emitting probe bodies 410 and 310, which are fixed to the probe holder 200, protrude inward (in the light-shielded space 501) larger than outward. For this reason, the portion protruding outward becomes small, so that it is possible to prevent something from being caught by the protrusion as much as possible. In particular, since the portion protruding outward is protected by the cap 700, it is possible to further resolve the above-mentioned problem and to improve the appearance.

In addition, in this embodiment, signal wiring is contained in the probe holder 200 and the detection and light-emitting probe bodies 410 and 310 are protected by the caps 700. Accordingly, it is possible to clear the appearance where a plurality of needles comes out and signal wiring stands by itself like in the related art, and to reduce the discomfort of the subject.

Meanwhile, the detection and light-emitting probe bodies 410 and 310 are disposed so that the upper portions of the detection and light-emitting probe bodies are held by the probe holder 200 and the detection and light-emitting probe bodies further protrude toward the light-shielded space 501. Further, the depth of the sheet holding unit 500 is set so that the tips of the main protrusions 412 provided at the tips of the detection and light-emitting probe bodies 410 and 310 come in contact with the head of the subject.

The detection and light-emitting probe bodies 410 and 310, which further protrude toward the light-shielded space 501, have a problem in that it is difficult to maintain postures where the tips of the main protrusions 412 come in contact with the head of the subject. In this embodiment, since the plurality of sub-protrusions 414 are provided around the main protrusion 412, the main protrusions 412 and the sub-protrusion 414 form the surface contact that is composed of the plurality of point contacts with the subject's scalp. Therefore, the detection light-emitting probe bodies 410 and 310 stand by themselves in right postures where the tips of the main protrusions 412 come in contact with the subject's scalp. As a result, it is possible to solve the above-mentioned problem.

That is, since four sub-protrusions 414 are provided on the concentric circles P1 and P2 of the main protrusion 412 at regular intervals, as shown in FIG. 10A, the sub-protrusions 414 can make the detection probe body 410 stand by itself on the scalp of the subject 50 in a perpendicular posture. Accordingly, since the detection optical fiber 413, which is provided on the axis Q1 of the main protrusion 412, can be in a perpendicular posture, it is possible to improve accuracy.

Furthermore, even though the detection and light-emitting probe bodies 410 and 310 are in inclined postures when the subject puts on the probe device, it is possible to change the postures of the detection and light-emitting probe bodies into the right postures by rotating the detection and light-emitting probe bodies. Conversely, in this embodiment, a gap between the probe holder 200 and the subject's scalp is increased by the sheet holding unit 500, so that a space used to control the postures of the detection and light-emitting probe bodies 410 and 310 is ensured.

That is, if the axis Q1 of the detection probe body 410 is in an inclined posture as shown in FIG. 10B when the subject 50 puts on the probe device 100, it is possible to make the axis Q1 of the detection probe body 410 be perpendicular and be in the perpendicular posture shown in FIG. 10A by grasping the cap 700 and rotating the first casing 421. In this case, it is possible to easily perform the posture control operation by using the cushion part 431. Further, as shown in FIG. 10B, if the sub-protrusion 414 is made of a soft material, the posture control operation is improved by using the elasticity of the sub-protrusion. In particular, since the detection optical fiber 413 is provided on the axial center of the main protrusion 412 in this embodiment, the main protrusion is harder than the sub-protrusion 414. Therefore, the posture control operation is improved by the rotation.

In this way, since a large light-shielded space 501 is ensured between the probe holder 200 and the subject's scalp in this embodiment, it is possible to ensure breathability, which improves the sweating of the subject, by the large space.

As shown in FIGS. 11A and 11B, in this embodiment, the head tightening structure has been employed to further improve the mountability of the probe device 100 on the subject. As shown in FIG. 11B, a tightening adapter 650 including wire hold protrusions 652 on both ends of a flat ring-shaped washer 651 is prepared in this embodiment, and is mounted on the flange 454 together with the probe holder 200, or the light-emitting and detection probes 300 and 400 of a middle stage are mounted when the cap 700 is mounted. Further, a wire mounting part 653 is provided at the sheet holding unit 500 on which the belts 601 are mounted, and a wire 654 passing through the wire mounting part 653 is mounted on the wire mounting part 653. With this structure, it is possible to press the entire middle portion of the probe holder 200 that is easily loosened.

Furthermore, in this embodiment, one end of each of the belts 601 is mounted to a slightly lower portion of the sheet holding unit 500. Accordingly, the belt fixing parts 602 are positioned at the rear of the subject's neck, so that the mountability of the sheet holding unit 500 is improved. In addition, in this embodiment, a second fixing band 610 may be mounted to a slightly upper portion of the sheet holding unit 500 as a unit for further improving the mountability of the probe device 100 (see portions shown by a broken line). With the second fixing band 610, it is possible to fix the probe device 100 at an upper portion of the head of the subject. Accordingly, when the two fixing bands are mounted, it is possible to reliably hold the probe device 100 by three points surrounding the head of the subject, that is, a front portion of the head with the sheet holding unit 500, a rear portion of the neck with the fixing band 600, and a rear upper portion of the head with the second fixing band 610. Therefore, it is effective during an action having the risk of separation.

Figure 12A:
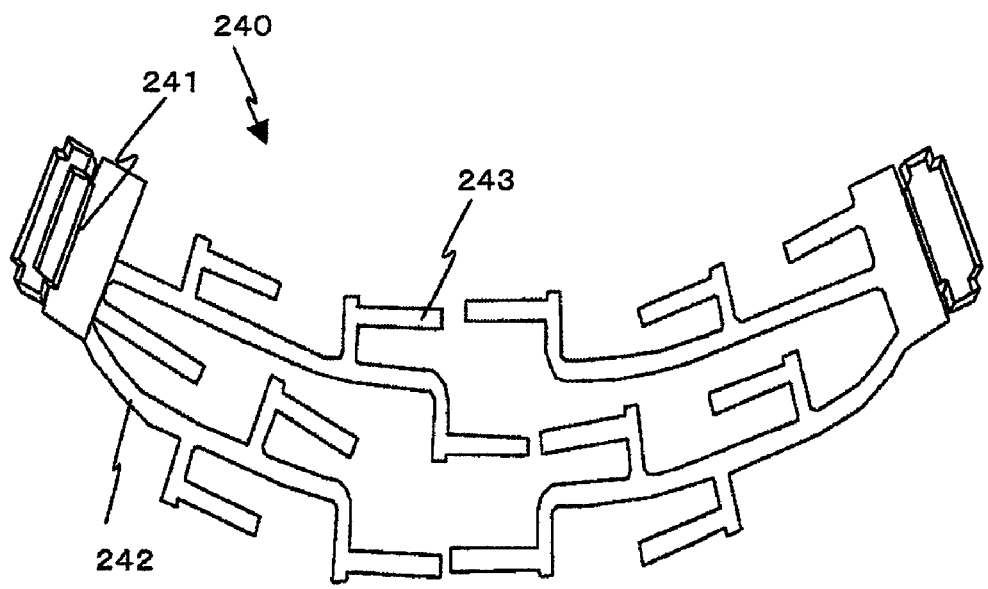
FIGS. 12A and 12B are external views showing an application of another wiring sheet.
Figure 12B:
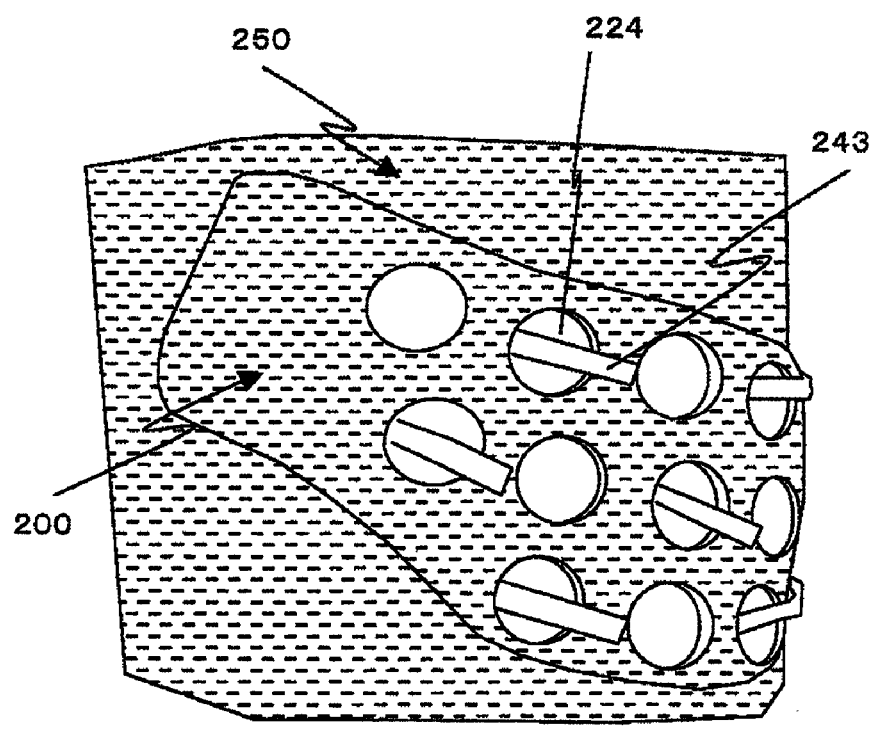

Next, another application of the probe device 100 according to this embodiment will be described below with reference to FIGS. 12A and 12B. FIGS. 12A and 12B are external views showing an application of another wiring sheet, and FIG. 12A is an external view of the wiring sheet, and FIG. 12B is a view showing that the wiring sheet is assembled.

In FIGS. 12A and 12B, a wiring sheet 240 according to this embodiment is a wiring sheet 240 for a probe device that introduces a light source generated outside of the probe device 100 into the light-emitting probe 300 through the optical fiber.

In the above-mentioned embodiment, it has been described that the light-emitting probe 300 employs the light emitting unit 311 provided with a light-emitting diode. However, a light-emitting probe body (not shown) to which an optical fiber for transmitting a light source generated outside is connected may be mounted instead of the light-emitting probe body 310 including the light emitting unit 311. In this case, if an optical fiber is wired instead of the connection terminal 230a, other structure does not need to be significantly changed. However, there is a problem in that an optical fiber is led to each of the light-emitting probes 300. In this case, if an adapter having the same structure as the tightening adapter 650 is provided and an optical fiber is mounted instead of a wire 654, it is possible to wire the optical fiber in order.

However, when a light-emitting probe body using an external light source is always used, the wiring sheet 230 wired in the probe holder 200 is not needed. The wiring sheet 240 shown in FIG. 12A on which the detection probes 400 are exclusively wired may be employed in this case.

Further, the wiring sheet 230 employed in the first embodiment and the wiring sheet 240 are formed along a spherical surface in advance so as to match the curved probe holder 200. This has been described for the wiring sheet 240, but the structure thereof may also be employed in the wiring sheet 230.

The probe device 100 according to this embodiment is formed to be curved to be fit to the shape of the spherical head of the subject. In particular, since having laminate structure and being curved, the probe holder 200 does need to be contrived. In this case, as shown in FIG. 12A, the wiring sheet 240 previously formed along a spherical surface may be employed in this embodiment.

The wiring sheet 240 is formed to have a pair of (left and right) structures like the wiring sheet 230. The wiring sheet 240 has the structure where several strip-shaped branch parts 242 are brought out from base parts 241 formed at the ends of the wiring sheet and the branch parts 242 are further branched out. The branched ends 243 are formed in a strip shape so as to be exposed to the openings 224 of the probe holder 200.

According to this embodiment, a curved mold (not shown) is previously prepared. Then, as shown in FIG. 3, the inner sheet 222, the light-shielding sheet 223, the wiring sheet 240, and the outer sheet 221 are provided in the mold in this order so as to be aligned using the openings 224, are laminated so that the branch parts 242 of the wiring sheet 240 are exposed to the openings 224, and are molded by thermal compression bonding. Since being made of fabrics, the inner sheet 222, the light-shielding sheet 223, and the outer sheet 221 may be easily changed from a flat sheet-like fabric into a cubic fabric during the molding. However, there is a problem in that a general wiring sheet on which wiring has been performed may not be subject to the molding and causes molding defects such as wrinkles. Meanwhile, the wiring sheet 240 according to this embodiment is previously molded along the spherical surface, and has the structure branched out into the plurality of pieces. Accordingly, it is possible to form a molded product 250 where the branch parts 242 are exposed to the openings 224 as shown in FIG. 12B. It is possible to form the probe holder 200 by cutting the periphery of this molded product 250.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A probe device used in a biological light measuring apparatus including a light radiation unit for radiating light on a biological surface and a light detection unit for measuring intensity of the light passing through a living body and emitted from the biological surface, said probe device comprising:
   a sheet-like probe holder;
   a plurality of light-emitting probes and a plurality of detection probes mounted on said probe holder at a predetermined interval;

a sheet holding unit is configured to hold said probe holder at a predetermined position on the biological surface; and a fixing band that is configured to mount said sheet holding unit on the living body, wherein each of said plurality of the light-emitting probes and the detection probes includes a probe body including a light emitting unit or a detection unit, and a probe mounting part detachably mounting said probe body to said probe holder at a predetermined position, said sheet holding unit surrounds a periphery of said probe holder, and has a predetermined gap between said probe holder and the biological surface so as to form a light-shielded space where light is shielded, said probe body includes a main protrusion provided with a light transmission unit, and a plurality of sub-protrusions disposed around said main protrusion, at one end thereof, said sub-protrusions having substantially the same length as that of said main protrusion and three or more sub-protrusions being provided around said main protrusion and said probe mounting part holds said probe body rotatably about said main protrusion so that one end of said probe body including the main protrusion and the sub-protrusions is exposed to said light-shielded space, the other end of said probe body is exposed to an outside of said probe holder, and the probe body rotates about the main protrusion, and a distance of a portion of said probe holder protruding toward said light-shielded space is larger than a distance of a portion of said probe holder protruding toward the outside.

2. The probe device according to claim 1,
wherein said probe holder is a laminate structure where a light-shielding sheet disposed between outer and inner sheets and a wiring sheet are laminated.

3. The probe device according to claim 1,
wherein said sheet holding unit includes an electrical substrate, and the electrical substrate is provided with a communication unit for wirelessly communicating with a biological light measuring apparatus body which performs image processing of an electric signal output from said probe device and displays the electric signal on a map, and a power source that supplies power to said probe device.

* * * * *